United States Patent [19]

Maechtle et al.

[11] 4,202,632
[45] May 13, 1980

[54] PROCESS AND APPARATUS FOR OPTICAL RECORDING OF MOTIONS AND STATES IN ULTRACENTRIFUGES IN MULTI-CELL OPERATION

[75] Inventors: Walter Maechtle, Ludwigshafen; Utz Klodwig, Mannheim, both of Fed. Rep. of Germany

[73] Assignee: BASF Aktiengesellschaft, Ludwigshafen, Fed. Rep. of Germany

[21] Appl. No.: 846,331

[22] Filed: Oct. 28, 1977

[30] Foreign Application Priority Data

Oct. 28, 1976 [DE] Fed. Rep. of Germany ....... 2649027

[51] Int. Cl.$^2$ .................................... G01N 21/24
[52] U.S. Cl. .................................. 356/427; 250/573; 356/442
[58] Field of Search .............. 356/198, 197, 23, 201, 356/25, 23, 426–428, 432, 442; 250/573

[56] References Cited

U.S. PATENT DOCUMENTS

| 1,904,124 | 4/1933 | Cockrell ................................. 356/25 |
| 3,599,002 | 8/1971 | Beutelspacher et al. ........ 356/197 X |
| 3,615,140 | 10/1971 | Doornekamp et al. ......... 356/427 X |
| 3,712,742 | 1/1973 | Cohen .................................. 356/427 |
| 3,758,949 | 9/1973 | Fausel et al. ............... 250/231 SE X |
| 3,970,967 | 7/1976 | Iliff .............................. 331/94.5 M X |

OTHER PUBLICATIONS

Stone, J. M., *Radiation and Optics*, McGraw-Hill, N.Y., 1963, pp. 455, 456.

Primary Examiner—F. L. Evans
Assistant Examiner—Bruce Y. Arnold
Attorney, Agent, or Firm—Keil & Witherspoon

[57] ABSTRACT

A method of measurement for analytical ultracentrifuges with a multi-cell rotor and with simultaneous measurement of several cells, in which light pulses of constant energy are passed, independently of the rotor speed, through individual selectable measuring cells in the entire speed range and in which these light pulses can be provided either by a controlled laser beam or a controlled Kerr cell or a controlled gas discharge lamp.

2 Claims, 4 Drawing Figures

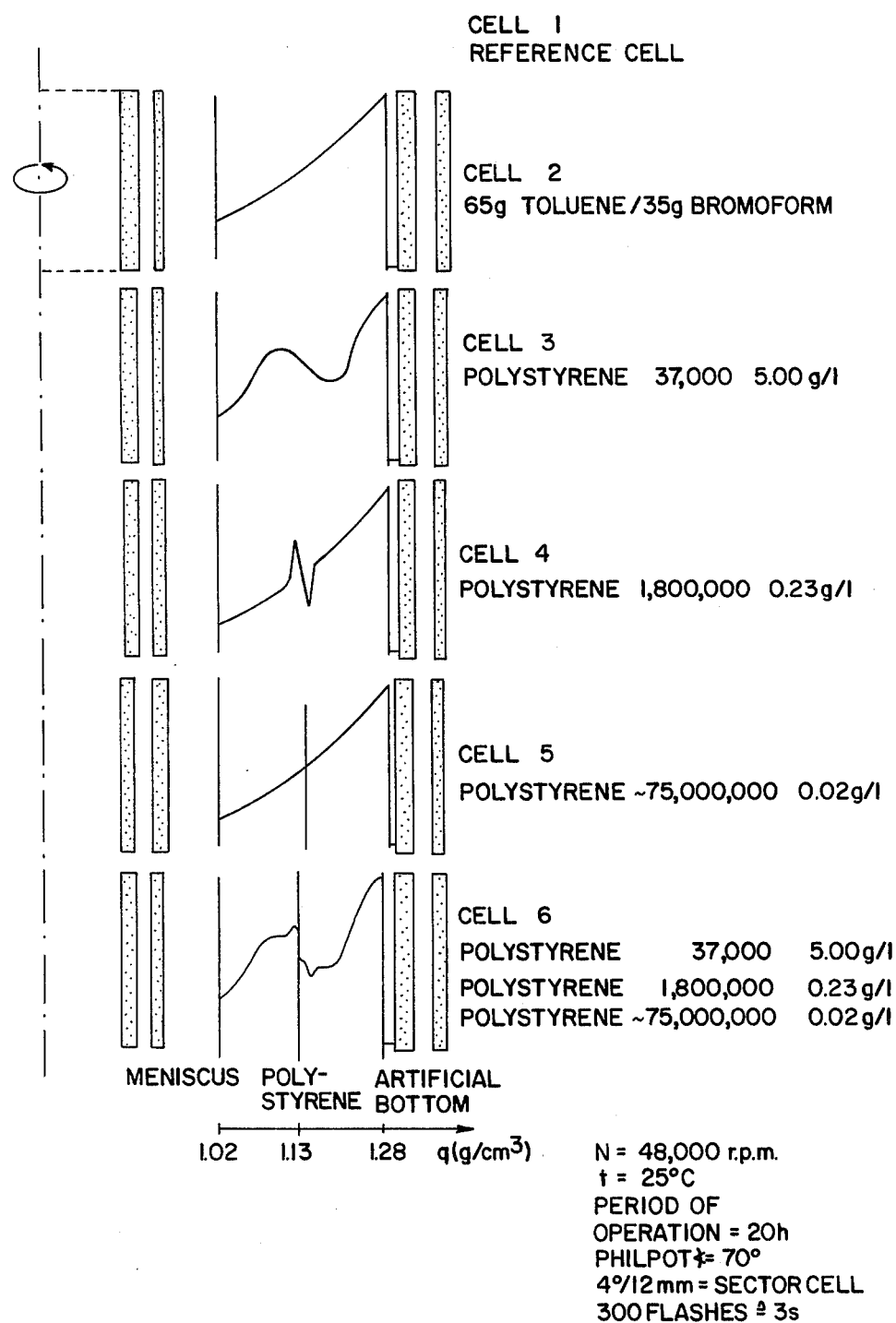

PROCESS AND APPARATUS FOR OPTICAL RECORDING OF MOTIONS AND STATES IN ULTRACENTRIFUGES IN MULTI-CELL OPERATION

The present invention relates to a process for the optical recording of motions and states, especially sedimentation phenomena and equilibrium states, in analytical ultracentrifuges and preparative ultracentrifuges with an analytical attachment, a plurality of cells in a multi-cell rotor being measured simultaneously, and to the various embodiments of apparatus for carrying out the process.

Methods for photographically recording sedimentation phenomena and equilibrium states of macromolecules and micro-particles in an ultracentrifuge have been disclosed; these include, for example, Schlieren optics, interference optics and absorption optics. Further, German Pat. No. 934,201 and German Laid-Open Application DOS 1,798,101 disclose multiplying the measuring capacity of ultracentrifuges with optical recording by changing from two-cell operation—that is to say one reference cell and one measuring cell per rotor, with the light source continuously switched on—to multi-cell operation. In multi-cell operation, a flash-light stroboscope shines through a reference cell and a plurality of measuring cells in one rotor. Using an inductive or a capacitive emitter inside the rotor chamber, consisting of fixed elements and of elements which revolve with the multi-cell rotor, and using an electronic control instrument outside the rotor chamber, the flash sequence of the stroboscope light source is controlled synchronously with the frequency of revolution of the rotor so that light is only emitted when a certain measuring cell passes through the optical path of the beam. By resetting the flash sequence from one cell to the next, all the cells can successively be inspected and photographed.

Multi-cell rotor operation of analytical ultracentrifuges with ultraviolet scanner recording instead of the above optics for photographic recording has also been disclosed. Here, the images of the cells are projected by means of a measuring beam with ultraviolet optics into the image plane of the scanner. In this plane there is a narrow slit which can be moved over the cell image by means of a spindle drive. Behind the slit there is a photomultiplier, to which a pen recorder is connected. On this, the absorbance of the ultraviolet light in the measuring cell is recorded as a function of the radial distance from the rotor axis. In the case of multi-cell rotor operation with ultraviolet scanner recording, two embodiments have been disclosed. In the case of one embodiment, described by C. H. CHERVENKA in Fractions, 1 (1971), pages 1 et seq., it is possible to select individual cells, with the light source continuously switched on, via an optical emitter in the rotor chamber by only switching on the output signal of the photomultiplier for a brief period when the preselected cell passes through the path of the ultraviolet measuring beam. In the other embodiment which has been disclosed (R. KUHNERT, E. RODEL, H. STEGEMANN and G. WASTL, CZ-Chemie-Technik 2 (1973), 441 et seq.) the photomultiplier output remains constantly switched on and a stroboscope light source is used which is controlled by an optical emitter located in the rotor chamber and only provides a light flash when the preselected cell passes through the path of the ultra-violet measuring beam.

However, it is a disadvantage that, for example, numerous synthetic polymers absorb insufficient light in the ultraviolet region so that an ultraviolet scanner cannot be employed. It is then necessary to resort to photographic recording by means of the above optics, which are based on differences in refractive index between the polymer solution and the pure solvent. Furthermore, with the conventional devices having an optical emitter within the rotor chamber high temperature measurements in the range up to 150° C., such as are needed, for example, for polyolefins, are not possible since the photoactive elements of an optical emitter are temperature-sensitive. On the other hand, the inductive or capacitive emitter which are more suitable for higher temperatures have the disadvantage that the control signals which they generate are relatively weak and prone to faults and that because of the residual induction of their ferromagnetic components phase shifts occur which depend on the rotor speed. By contrast, optical emitters do not show any dependence on the speed of rotation and can provide powerful electrical control signals. The energy of the individual light flashes of a stroboscope flashlight is also very frequency-dependent in the range from $0 < n < 80,000$ rpm. This is a disadvantage since in such a case different flash numbers are required, at different rotor speeds, for the optical exposure of a photographic plate, which makes automatic exposure very much more difficult.

A further disadvantage of the conventional recording devices for multi-cell operation is that in place of the conventional multi-cell rotors, special multi-cell rotors are used which in part possess additional holes for optical emitters or special control cams or control electrodes for inductive or capacitive emitters. The tensile strength of the rotors, or their maximum permissible speed, may be reduced by the presence of these holes so that the rotors can no longer be employed for extreme duties. When using inductive or capacitive emitters inside the rotor chamber, laborious adjustments of the distance between the fixed elements and of the elements which revolve with the rotor are necessary. If the rotor runs insteadily for example in a critical speed range or, in the case of nutation, due to being out of balance or due to uneven loading or due to emptying of a cell during running, and the like, inductive or capacitive emitters therefore tend to give untidy control signals. Optical emitters are less prone to faults in this respect.

The photographing of individual measuring cells in immediate succession onto separate photographic plates, as practised in multi-cell operation, is also unsuitable for measurements of maximum accuracy because the entire process takes too much time. This applies particularly to Schlieren-optics photographs if it is required that, in addition to the Schlieren line of an individual solution, the Schlieren base line of the pure solvent and the two lines of the reference cell must be present on the same photograph in order to permit precise planimetric measurement of the peak area even at high rotor speeds at which the Schlieren base line is frequently not straight but curved. If the entire recording process takes a long time, the states of sedimentation of the individual samples in the various measuring cells are no longer identical. This results in the further requirement that an improved measuring instrument for analytical ultracentrifuges should allow two or more cells to be recorded simultaneously on one photographic plate, for example by alternately passing the beam through these cells. In the case of the Schlieren-optics recording of density gradient runs, the preferred combination for superposed images would be: solution cell/solvent cell/reference cell. Passing the beam alternately through several cells would result in a great improvement in the accuracy of measurement. Particularly where samples only differ slightly in molecular weight and in particular specific volume, superposed images would show small differences which are not visible in separately taken photographs.

Accordingly, it is an object of the present invention to provide a process and apparatus for photographic recording in ultracentrifuges with multi-cell rotor operation which simultaneously conform to the following requirements:

(a) The light energy which is allowed through a cell by the optical interruptor, per switching sequence, should be constant and should in particular be independent of the rotor speed.

(b) The switching synchronization of the optical interruptor should be independent of the rotor speed and should operate automatically over the entire speed range, even in the case of rapid changes in speed.

(c) Any device for carrying out the process should make it possible, by means of an optical interruptor which is controlled via a reliable optical emitter, to examine both individual cells and the superposed images of several cells.

(d) The optical emitter should be located entirely outside the rotor chamber to permit high temperature measurements.

(e) It should be possible to fit a device according to the invention subsequently into existing commercial analytical ultracentrifuges and into preparative ultracentrifuges with an analytical attachment, without requiring special rotors or special cells in the existing rotors.

According to the invention this complex object is achieved by a process wherein the measuring cells are illuminated, over the entire speed range of from 100 to 80,000 rpm, with light pulses of constant energy which are independent of the speed. According to a further feature of the invention, the light pulses of constant energy are provided either by a controlled laser beam or a controlled Kerr cell or a stroboscope flashlight which is charge-controlled via a capacitor.

An apparatus for carrying out the process is in particular distinguished by the combination of the following features, regardless of the light source used:

(a) one or more optical interruptors, located outside the rotor chamber and operating synchronously with the frequency of rotation of the rotor in one beam path through the rotor chamber, for the controlled activation of the corresponding light source, (b) an optical emitter, fixed outside the rotor chamber and essentially comprising a light source, diaphragm and lenses, which acts on a phototransistor in a second beam path parallel to the first beam path through the rotor chamber, (c) an electrical control and synchronizing instrument with preselector switches for a given cell, which receives the pulses provided by the optical emitter according to (b) and by means of which the number of sequences, which determines the exposure time of the photographic plate of the ultracentrifuge, can be preselected as required for each cell of the rotor.

BRIEF DESCRIPTION OF THE DRAWINGS

Further features of the invention will be apparent from the following detailed description when taken in conjunction with FIGS. 1 to 4 of the accompanying drawing in which:

FIGS. 3 and 4 show Schleiren photographs resulting from various measurements taken with the apparatus according to the invention.

Figure 1:
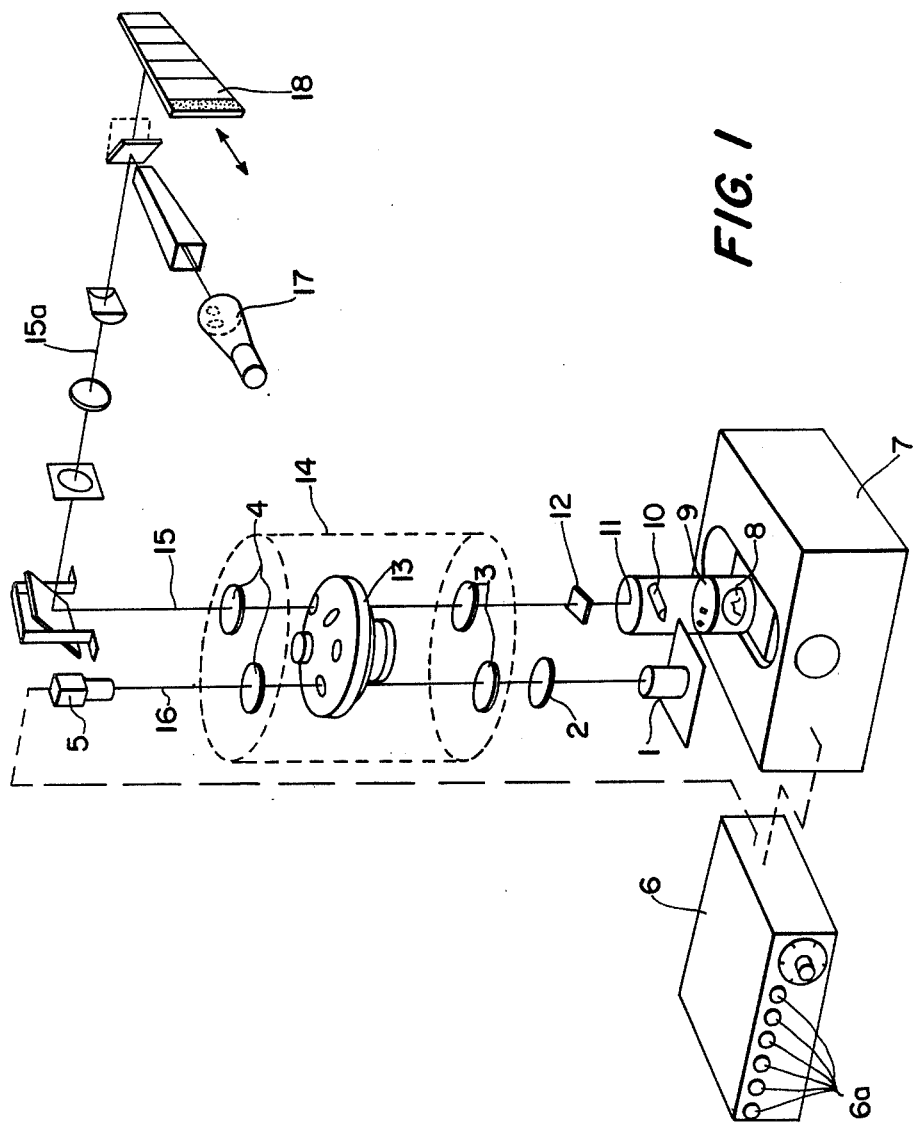
FIG. 1 gives an overall perspective view of the apparatus according to the invention and shows, diagrammatically, the rotor chamber and rotor, the beam paths, the interruptor, the control instrument and the recording device with photographic plate.

The optical interruptor for one or more measuring beam paths 15, 15a essentially comprises the unit 7 for the voltage supply, a controlled lamp 8, a focusing lens 9 and a cylindrical lens 10. If several measuring beam paths 15 are provided, such an interruptor 7 to 10 is located in each of these beam paths. Each individual beam path and the corresponding interruptor can then, for example, employ measuring light of a different wavelength. Each interruptor ensures, synchronously with the rotational frequency of the multi-cell rotor 13, that a constant light energy is provided, for a consistently constant, short period of time (which should however advantageously be less than 10 microseconds) while an individual measuring cell passes through the path (15) of the measuring beam; the interruptor achieves this as follows:

(a) with the lamp 8 switched on continuously, the interruptor only opens the beam path 15 within the predetermined short period or (b) with a lamp 8 which can be switched on in a pulse-like manner, the interruptor only switches on the lamp for the predetermined short period, the light energy emitted per pulse always remaining constant, i.e. independent of the number of sequences.

A constant duration of 10 microseconds or less should be chosen so that at the maximum rotor speed the minimum time of passage of a measuring cell through the path of the measuring beam 15 is adequately longer than 10 microseconds. The constancy of either the period for which the path of the measuring beam 15 is open, in embodiment (a), or the constancy of the light energy per light pulse, in embodiment (b), is the precondition for simple automatic exposure. To achieve photographic plates 18, which have received optimum exposure, at the far end of the deflected measuring beam path 15a it then merely remains necessary to set the appropriate number of sequences, depending on the sensitivity of the plates, on a flash number preselector counter of the electronic control instrument 6; this will be dealt with in more detail below, in relation to FIG. 2.

The optical interruptor 7 to 10 can for example be, as shown diagrammatically in FIG. 1, a rapidly controllable pulsed gas discharge lamp 8 (stroboscope flashlight), in which case focusing optics, comprising a focusing lens 9 and a cylindrical lens 10, are essential for intensive illumination of the slit 11 of the measuring optics. On the other hand, the optical interruptor can consist of a laser—acting as the light source 8—which can be rapidly controlled in the form of pulses, in which case a filter or the monochromator 12 can be dispensed with. According to a further embodiment within the scope of the invention, the interruptor 7 to 10 can also be provided by retaining the conventional continuously switched-on mercury vapor lamp as the light source 8 and inserting a rapidly controllable optical shutter, for example a Kerr cell, in the beam path 15 at a suitable point between the light source 8 and the photographic plate 18 at the far end of the deflected measuring beam path 15a.

In the event of using a gas discharge lamp or a laser controllable in the form of pulses, the unit 7 must be of such construction that it ensures, by electronic means, that the light energy of the light pulses is constant at all possible switching frequencies and over the entire speed range of the rotor. In order to guarantee this constancy of the light flash energy and also to increase the life of the interruptor 7 to 10, it can be advantageous, at very high rotor speed, no longer to trigger a flash for each revolution but instead only for every second or third revolution and so on. This is achievable by allowing the trigger pulses transmitted by the electronic control instrument 6 to the optical interruptor 7 to 10 additionally to pass, within the control instrument 6, through a monostable multivibrator which only transmits pulses which occur at a time interval greater than a fixed predetermined period. If, for example, this time is 0.01 second, and the rotor speed is 60,000 rpm, a flash is provided for only every tenth revolution of the rotor.

The optical emitter is arranged with its essential parts outside the rotor chamber 14 in order to permit high temperature measurements in the interior of the chamber. As shown in FIG. 1, the beam path 16 of the optical emitter comprises a filament lamp 1, a diaphragm 2, one or more collimating lenses 3, a corresponding number of condenser lenses 4 and a phototransistor 5, the output of which is connected to the control instrument 6. With this type of construction and arrangement of the optical emitter it is not necessary to make any mechanical changes to commercial multi-cell rotors 13, which is advantageous since such changes could interfere with the good running characteristics of the rotor, especially at the maximum speeds to be employed.

The purpose of the optical emitter 1 to 5 is to provide, with the aid of a standard reference cell located in the rotor 13, an unambigous, pulse-shaped, electrical control signal per revolution of the rotor, this signal being passed to the electronic control instrument 6. The reference cell must be run in the rotor for each measurement in order to be able to determine the absolute cell radii. For the purposes of the invention, this requirement is met by the fact that the optical emitter comprising the elements 1 to 5 is located, parallel to the measuring beam path 15, in the control beam path 16, this latter path being at the same distance from the rotor axis as is the measuring beam path. Hence, the control beam path 16 also passes through the centers of the holes for the cells in the rotor 13. At the points at which the control beam path 16 passes through the walls of the rotor chamber 14, vacuum-tight plane-parallel windows or lenses 3, 4 have to be provided unless these are already present, as is the case with more recent equipment. The filament lamp 1 which is employed is preferably a voltage-stabilized, continuously burning low voltage filament lamp at the focal point of the collimating lens 3, with an interposed edge-type diaphragm 2. This diaphragm 2 only allows part of the total beam from the filament lamp 1 to enter the rotor chamber 14; this part-beam passes through one of the holes of the reference cell. Because of the edge-type diaphragm 2, light from the filament lamp cannot enter through the second hole of the reference cell or through the sector-shaped holes of all the measuring cells. Accordingly, the phototransistor 5, as required, always only provides one unambiguous electric pulse to the control instrument 6 per revolution of the rotor.

Figure 2:
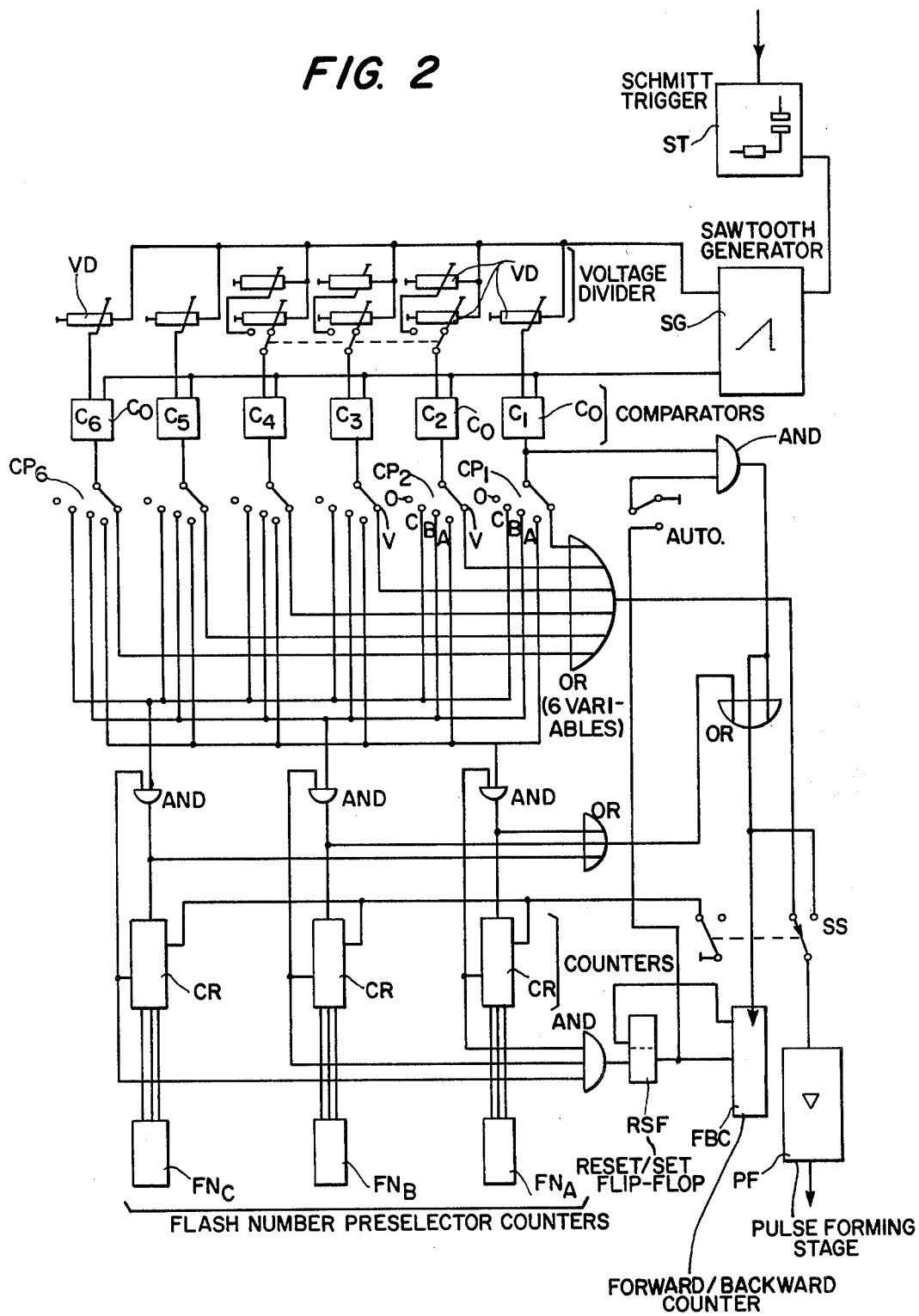
FIG. 2 shows in block diagram form the the circuit of the control instrument.

The electronic control instrument 6, the block circuit diagram of which is shown in FIG. 2, serves automatically to control the optical interruptor 7 to 10, by means of the pulses provided by the optical emitter 1 to 5, via preselector switches 6a for the cell number, the preselected number of sequences and the type of rotor used, in such a way that either (a) at all times only one preselected cell is illuminated or
(b) any two or more preselected cells are illuminated alternately in immediate succession, in order to produce, in the observation eyepiece 17 on the angled branch 15a of the measuring beam path 15, the superposed images of these cells, and/or to record them on the photographic plate 18.

In addition, the number of sequences which determines the illumination intensity is preselected, in the control instrument 6, on flash number preselector counters, thereby determining the exposure time of the photographic plate 18, both in the case of individual cell measurements and in the case of alternate exposure of several cells. Finally, an appropriate preselection is made on the control instrument 6 for each type of rotor, i.e. a 2-, 4-, 6- or 8-cell rotor.

FIG. 2 shows, in the form of a block circuit diagram, one of the possible embodiments of the control instrument 6, by means of which two-, four- or six-cell rotors can be run. The cell $C_1$ is always the reference cell and, in automatic operation, at most three cells A, B and C chosen at will can, in a cycle, be alternately flash-illuminated. With this automatic sequence, the reference cell is flash-illuminated by itself immediately following the alternating flash-illuminations, the number of flashes received by the reference cell corresponding to the sum of the flashes employed in the alternate flash illumination. The F/B (forward/backward) counter FBC ensures, in conjunction with an R/S Flipflop RSF (Reset/Set Flipflop=bistable multivibrator) that the number of flashes applied to the reference cell is equal to the sum of the number of flashes set on the three flash number preselector counters $FN_A$, $FN_B$ and $FN_C$. In addition to the automatic sequence with its limited flash number, it is also possible, for visual operation, to provide flashes of unlimited duration, either individually or in cyclic alternation, by bringing the 5-pole cell preselector switch $CP_1$–$CP_6$, allotted to each cell, into position V (=visual).

The description which follows of the construction, according to the invention, of the control instrument 6, and of its mode of action, shows the substantially extended scope for measurements compared to the conventional photographic recording techniques. The voltage pulses supplied by the optical emitter 1–5 to the input of the control instrument 6 first pass through a Schmitt trigger with a differential element, thus acquiring a defined form. The time interval between two such pulses is identical with the time which the rotor 13 requires for one revolution. Within this time, a capacitor is charged, strictly linearly, inside a saw-tooth generator, and this capacitor is rapidly discharged at the end of the time, so that a saw-tooth-like voltage leaves the saw-tooth generator, the maximum voltage of each saw-tooth always being identical, regardless of a change in the rotor speed over the entire speed range.

The constancy of the maximum saw-tooth voltage is achieved by additionally integrating into the circuit, with the saw-tooth generator SG, a comparator, a sample-hold amplifier and a difference amplifier. The voltage pulses of defined form coming from the Schmitt trigger ST are used, in the saw-tooth generator SG, on the one hand for rapid discharge of the saw-tooth capacitor with an FET switch (Field-Effect-Transistor switch) and, on the other hand, for triggering the sample-hold amplifier. From the output of the sample-hold amplifier, the maximum value of the saw-tooth is compared, in the comparator, with a fixed predetermined voltage of 10 V, and the voltage difference is amplified in an amplifier with a high time constant (=integrator) and is used to regulate the saw-tooth, so that the maximum saw-tooth voltage always remains the same independently of the rotor speed.

The absolute magnitude of the saw-tooth voltage is accordingly a measure of the angular position of the rotor 13 relative to the control beam path 16. Defined constant component voltages can be allotted to the constant angular positions of the various measuring cells of the rotor 13 relative to the reference cell $C_1$ and these component voltages are taken off a voltage divider VD—which follows the saw-tooth generator— with a number of tappings (contacts) corresponding to the cell number of the multi-cell rotor used. The cell number can be set on the preselector switch for the type of rotor. A constant voltage, identical with the maximum saw-tooth voltage, is always applied to the voltage divider VD. A tapped-off component voltage which corresponds to a measuring cell selected on the cell preselector switch CP is now compared, in a comparator CO, with the rising saw-tooth voltage. Each cell $C_1$-$C_6$ has allotted to it such a comparator CO, which also contains the monostable multivibrator referred to above, which only allows pulses at time intervals greater than a fixed predetermined time to pass through the comparator. At the instant at which the rising saw-tooth voltage becomes exactly equal to the predetermined component voltage of the preselected measuring cell, the comparator CO provides a triggering pulse to activate the optical interruptor 7 to 10 in the measuring beam path 15.

If the cell preselector switch CP of the corresponding measuring cell is set to V (=visual observation), the trigger pulse is fed—if the start-stop switch 0 is in the correct position—via an OR-gate and a pulse-forming stage PF from the output of the control instrument 6 directly to the optical interruptor 7 to 10. The OR-gate is required in order to regulate the sequence of the trigger pulses if cyclic alternate flashing is requred for visual observation, i.e. if several cell preselector switches are simultaneously in position V.

In the case of an automatic flashing sequence, the cell preselector switches CP of the measuring cells which are to be flash-illuminated in cyclic alternation—a maximum of three is shown in FIG. 2—are brought into the three different positions A, B and C and the desired flash numbers are set on the flash number preselector counters $FN_A$, $FN_B$ and $FN_C$. The cell preselector switches CP of the cells which are not to be flash-illuminated must be brought to position O. The automatic switch must be turned off. The trigger pulses leaving the comparators then travel first to an AND-gate and a counter CR, where they are counted and compared with the flash number set on the flash number preselector counters $FN_A$, $FN_B$ and $FN_C$. The AND-gate remains open until the selected flash number is reached. Both in the case of visual observation and in the case of the automatic sequence the trigger pulses leave the output of the control instrument 6 via the same pulse-forming stage PF. Pressing the Start-Stop switch SS triggers a complete automatic sequence. With cyclically alternating illumination, a superposed image of the cells is produced as shown, for example, on the right of FIG. 3. In order to avoid over-exposure with such superposed images it is frequently advantageous not to illuminate all the measuring cells of the rotor 13 with equal frequency, but with different frequency. To achieve good photographic records, the less important cells, e.g. the solvent cell which produces the Schlieren base line, are illuminated less often. This is achieved in a simple manner by setting the flash number preselector counters $FN_A$-$FN_C$ of the control instrument 6 to different numbers of sequences for the various cells $C_1$-$C_6$, the images of which are to be superposed.

Figure 3:
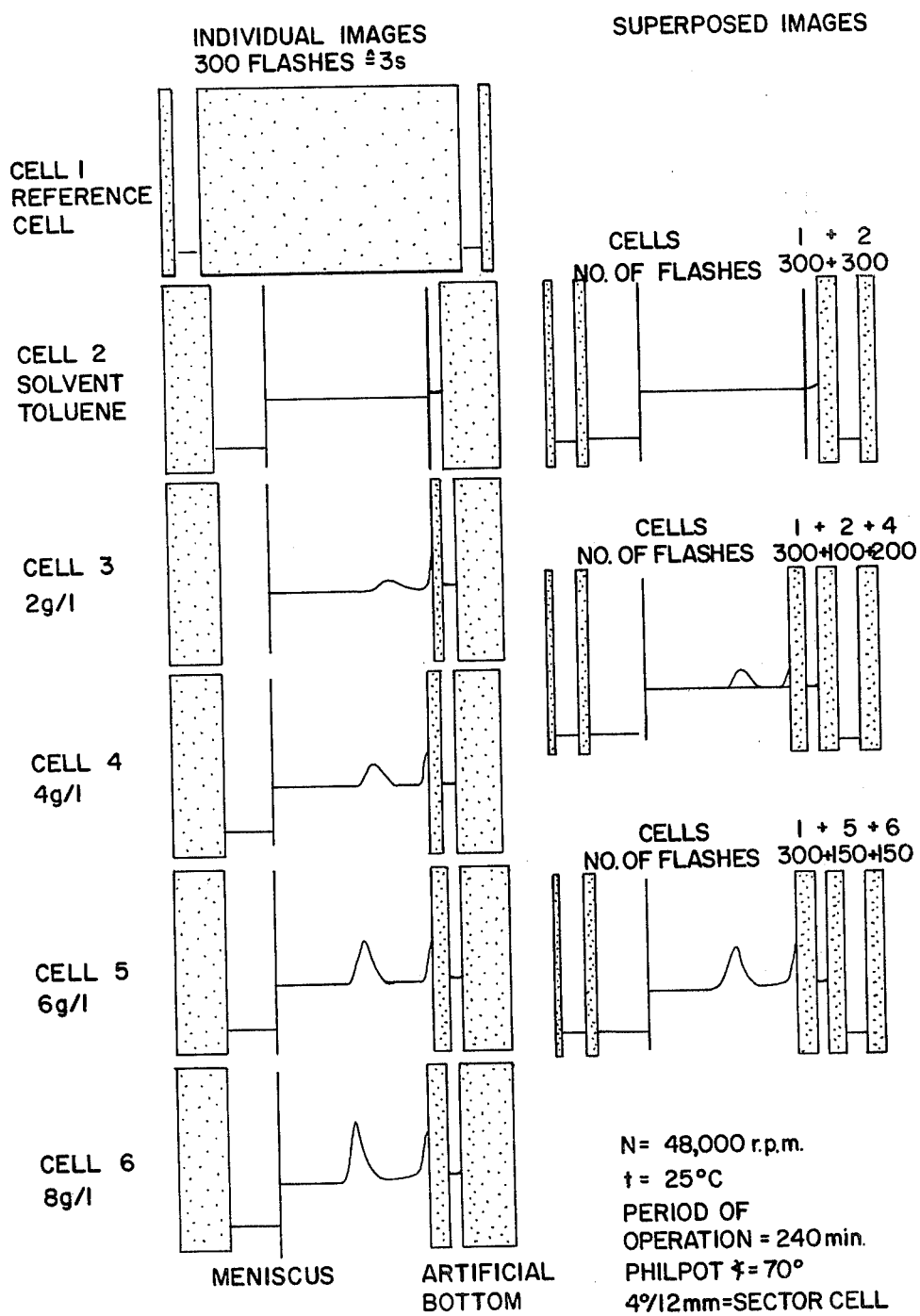

For photographing the two examples of measurements shown in FIGS. 3 and 4, the flash frequency was confined to the range from 0 to at most 100 cycles/second. Referring now to FIG. 1, unit 7 provided a constant flash energy of 1 Joule. The half-life of the flashes was in every case less than 2 microseconds. Hence, 300 flashes per photograph were required for satisfactory exposure of a commercial photographic plate 18. At the maximum flash frequency, this corresponds to an exposure time of 3 seconds.

FIG. 3 depicts, by way of an example of the measurements, Schlieren photographs which were taken during a sedimentation run with solutions, of various concentration, of a monodisperse polystyrene having a molecular weight M=110,000 g/mole. After a total running time of 240 minutes, all the photographs shown in FIG. 3 were taken in immediate succession, requiring a total of 3 minutes.

The examples of measurement shown in FIG. 4 correspond to Schlieren photographs of a density gradient run after allowing a time of 20 hours to reach equilibrium. Using a gradient mixture of 65 g of toluene and 35 g of bromoform as the solvent, three polystyrenes of different molecular weight, namely $M_1$=37,000, $M_2$=1,800,000 and $M_3$=about 75,000,000 (=cross-linked, spherical microgel particles) were measured individually and as a 1:1:1 mixture. FIG. 4 clearly shows the same density position of the three polystyrene bands and their increasing diffusion spread with decreasing molecular weight. With conventional operation, 7 working days would have been required for the same measurements. Accordingly, the ultracentrifuge constructed in accordance with the invention greatly increases the measuring capacity and hence permits substantially more economical use of this expensive equipment.

We claim:

1. A process for the optical measurement and recording of motions in ultracentrifuges having a multi-cell rotor for substantially simultaneously measuring a plurality of cells, said process comprising the steps of:
providing synchronizing pulses in accordance with the rotation of said rotor;

deriving from said synchronizing pulses light pulses of constant energy, said energy being independent of the rotational speed of said rotor within a range of from 100 to 80,000 revolutions per minute.

said light pulses being produced by a gas discharge lamp and said deriving step including linearly charging the capacitor of a saw-tooth generator, and rapidly discharging said capacitor at the end of the time interval between any two successive synchronizing pulses so that the maximum voltage of each saw-tooth of the saw-tooth wave produced by said generator is constant regardless of the rotor speed within said range, whereby light pulses of constant energy are obtained for said gas discharge lamp; and passing said light pulses through one or more cells to be measured.

2. An apparatus for the optical measurement and recording of motions and states, comprising an ultracentrifuge having a multi-cell rotor and a rotor chamber surrounding the rotor, means for emitting at least one beam of light for passage through at least one cell of the rotor, means located outside the rotor chamber adapted to operate synchronously with the speed of rotation of the rotor for interrupting the path(s) of said at least one light beam, an optical emitter comprising a light source fixed outside the rotor chamber, a diaphragm, lenses, and a phototransistor, the light source being adapted to emit a second beam along a path which is parallel, through the rotor chamber, to the path(s) of the beam(s) emitted by said light emitting means, and an electrical control and synchronizing instrument with preselector switches for one or more given cells, said instrument being adapted to receive pulses provided by the optical emitter for preselecting, at will, for each individual cell of the rotor, the number of sequences of the optical interruptor which determines the exposure time of the photographic plate.

* * * * *